US00PP33013P3

(12) United States Plant Patent
Ponson et al.

(10) Patent No.: US PP33,013 P3
(45) Date of Patent: May 4, 2021

(54) BLUEBERRY PLANT NAMED 'FLR12-11'

(50) Latin Name: ***Vaccinium corymbosum* L.**
Varietal Denomination: FLR12-11

(71) Applicant: Florida Foundation Seed Producers, Inc., Marianna, FL (US)

(72) Inventors: Sophie Ponson, Seville (ES); James W. Olmstead, Aptos, CA (US); Jean Clement Marcaillou, Seville (ES); Patricio R. Munoz Del Valle, Gainesville, FL (US); Jacques Kouadio, Seville (ES)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/923,942

(22) Filed: Jul. 8, 2020

(65) Prior Publication Data

US 2021/0015013 P1 Jan. 14, 2021

(30) Foreign Application Priority Data

Jul. 9, 2019 (EP) ..... 20191681

(51) Int. Cl.
*A01H 6/36* (2018.01)
*A01H 5/08* (2018.01)

(52) U.S. Cl.
USPC ..... Plt./157
CPC ..... *A01H 6/368* (2018.05)

(58) Field of Classification Search
USPC ..... Plt./157
See application file for complete search history.

(56) References Cited

U.S. PATENT DOCUMENTS

PP12,165 P2 10/2001 Lyrene
PP19,503 P3 11/2008 Lyrene

FOREIGN PATENT DOCUMENTS

EP 20191680 7/2019
EP 20191682 7/2019

OTHER PUBLICATIONS

U.S. Appl. No. 16/923,952, filed Jul. 8, 2020, Ponson et al.
U.S. Appl. No. 16/923,960, filed Jul. 8, 2020, Ponson et al.

*Primary Examiner* — Annette H Para
(74) *Attorney, Agent, or Firm* — Dentons US LLP

(57) ABSTRACT

'FLR12-11' is a new and distinct southern highbush blueberry (*Vaccinium corymbosum* L.) variety distinguished by a low chilling requirement, semi-upright growth habit, and large, firm fruit that are aromatic with a small, dry picking scar.

5 Drawing Sheets

Latin name of the genus and species of the plant claimed: *Vaccinium corymbosum* L.

Variety denomination: 'FLR12-11'.

CROSS REFERENCE TO RELATED APPLICATIONS

This application claims the benefit of European Community Plant Breeders Rights Appl. No. 20191681, filed Jul. 9, 2019, herein incorporated by reference in its entirety.

BACKGROUND OF THE INVENTION

The present invention relates to a new and distinct hybrid variety of southern highbush blueberry (*Vaccinium corymbosum* L.) named 'FLR12-11'. 'FLR12-11' is a blueberry clone distinguished by its very low chilling requirement, very good performance when grown in an evergreen production system, early ripening, and high production of large berries with excellent flavor. Several thousand plants of 'FLR12-11' have been propagated and established in Lalla Mimouna, Morocco, and the resulting plants have all been phenotypically indistinguishable from the original plant. 'FLR12-11' originated as a seedling from a cross between 'Snowchaser' as the female (seed) parent and 'Emerald' (U.S. Plant Pat. No. 12,165) as the male (pollen) parent. This cross was made in Lalla Mimouna, Morocco in 2012. The seedling was planted in a high-density field nursery in 2014 and the first fruit were evaluated during the same year. Due to its early fruit production and excellent fruit quality, 'FLR12-11' was selected and first asexually propagated in Lalla Mimouna, Morocco by softwood stem cuttings. In 2015, an experimental 10-plant test plot was established as part of a variety test at Lalla Mimouna Morocco. Based on the growth, yield, and fruit quality of this plot, 'FLR12-11' was repropagated by softwood stem cuttings and in 2016 experimental test plots were established at two other farms in Morocco. These plots have been observed during flowering and ripening each year, and no mutations or off-type plants have been observed.

'Snowchaser' (U.S. Plant Pat. No. 19,503) is an important southern highbush blueberry variety widely planted in the United States. 'FLR12-11' is believed to be most similar to 'Snowchaser'. Nonetheless, 'FLR12-11' and 'Snowchaser' are distinguishable at least in their fruit production, leaf shape, and leaf pubescence at the margins. Specifically, the volume of fruit (kg/plant) produced by the claimed plant is roughly forty-five percent (45%) greater than 'Snowchaser'.

The fruit of 'FLR12-11' is also twice as large as the fruit of 'Snowchaser' throughout the harvest season. Additionally, 'FLR12-11' exhibits an elliptic leaf shape with an absence of leaf pubescence at the margins, while 'Snowchaser' exhibits an ovate leaf shape with sessile glands along the margins of the leaf blade.

SUMMARY OF THE INVENTION

Blueberry variety 'FLR12-11' exhibits outstanding and distinguishing characteristics when grown under normal horticultural practices in Lalla Mimouna, Morocco, including: (1) a very low chilling requirement; (2) very good performance as an evergreen plant; (3) early fruit ripening; and (4) high production of large berries with an excellent, aromatic flavor.

BRIEF DESCRIPTION OF THE DRAWINGS

The accompanying photographs show typical bush, flower, and fruit characteristics for 'FLR12-11'. Colors shown are as true as can be reasonably reproduced by photographic procedures and may differ from those cited in the detailed description, which accurately describes the colors of 'FLR12-11'.

DETAILED BOTANICAL DESCRIPTION

Figure 1:
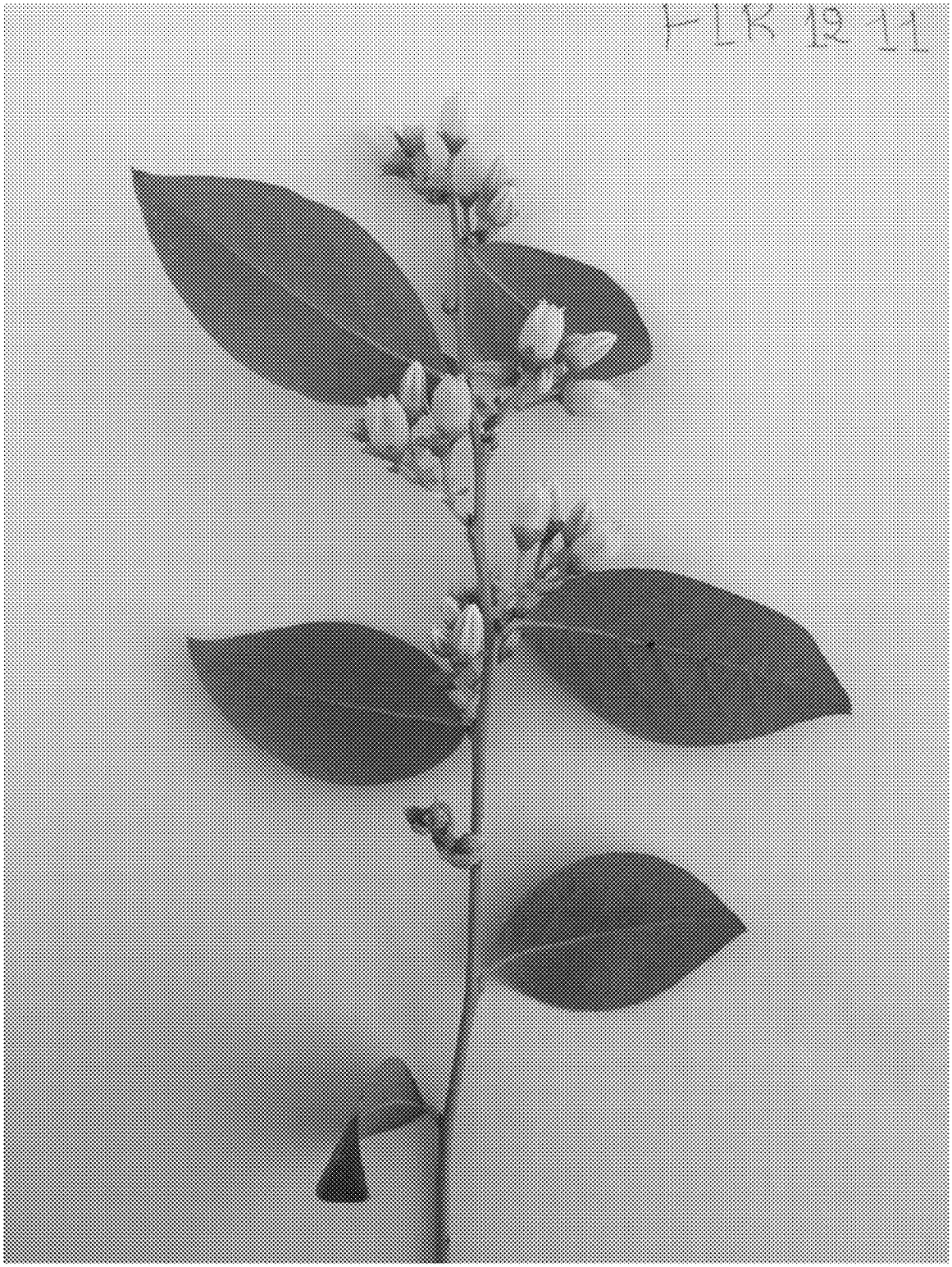
FIG. 1—Shows several clusters of flowers of 'FLR12-11', as observed during flowering in March.
Figure 2:
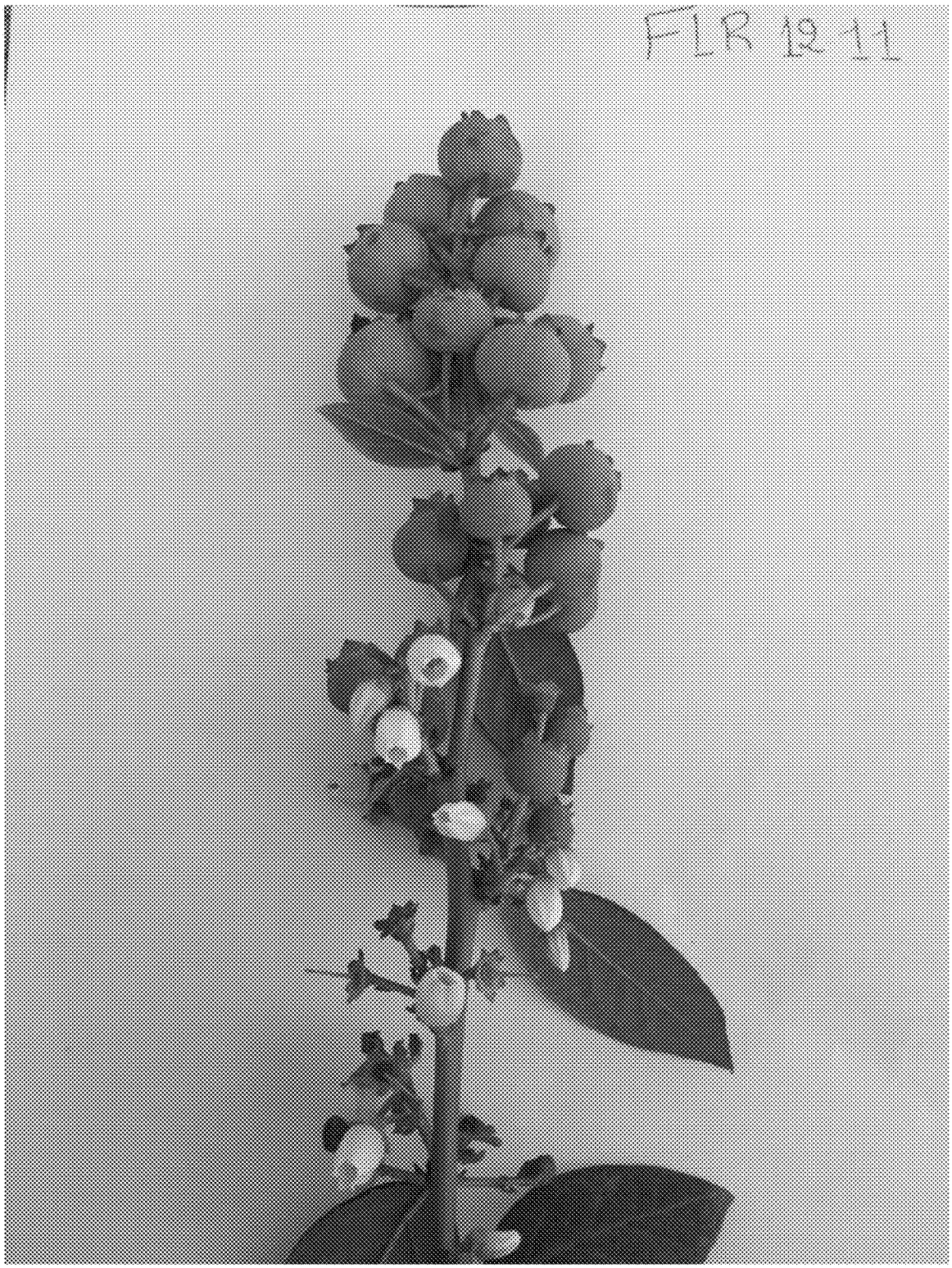
FIG. 2—Shows branches with green fruit of 'FLR12-11' during the fruit ripening period.
Figure 3:
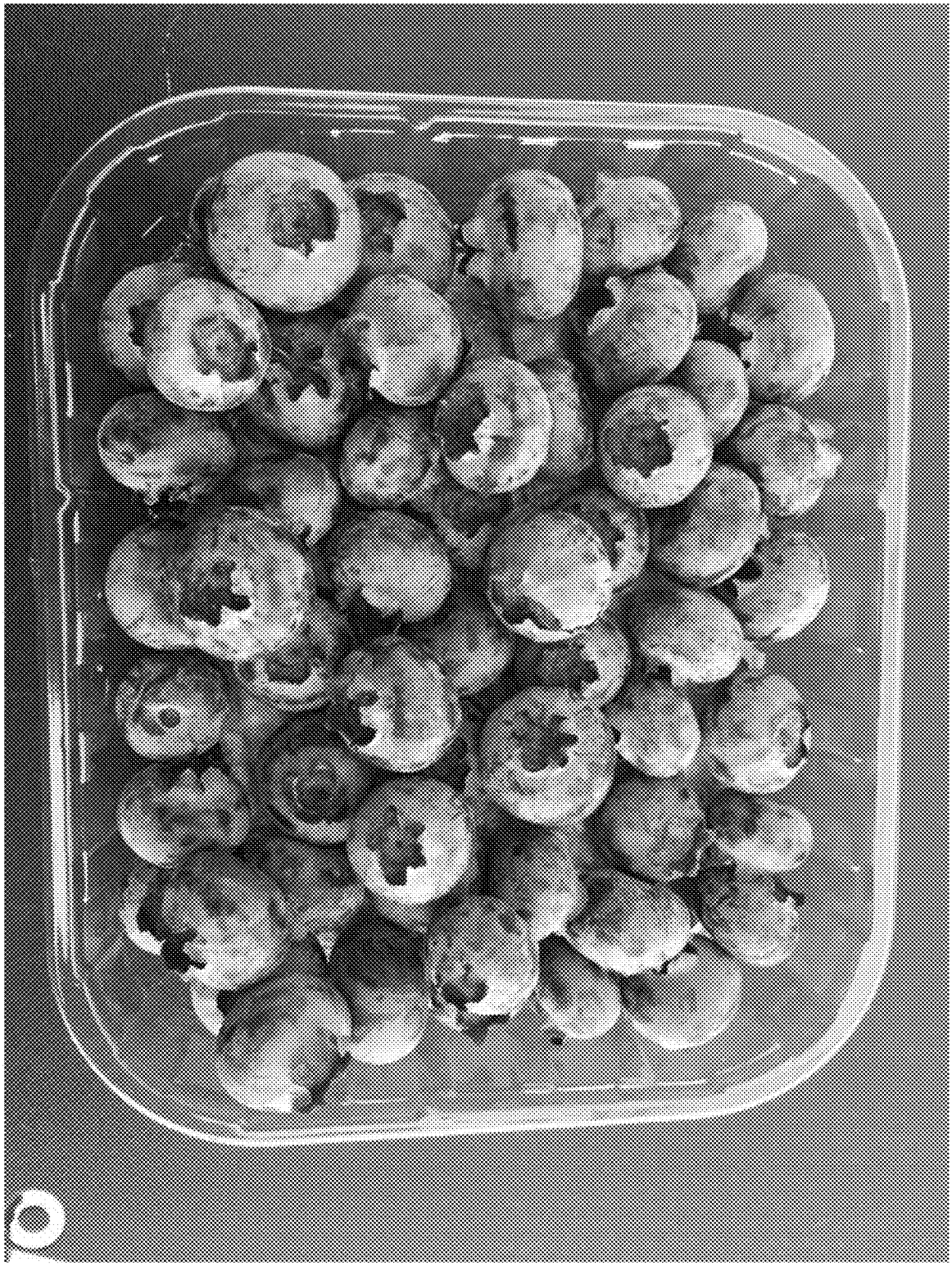
FIG. 3—Shows a close-up of harvested 'FLR12-11' ripe berries.
Figure 4:
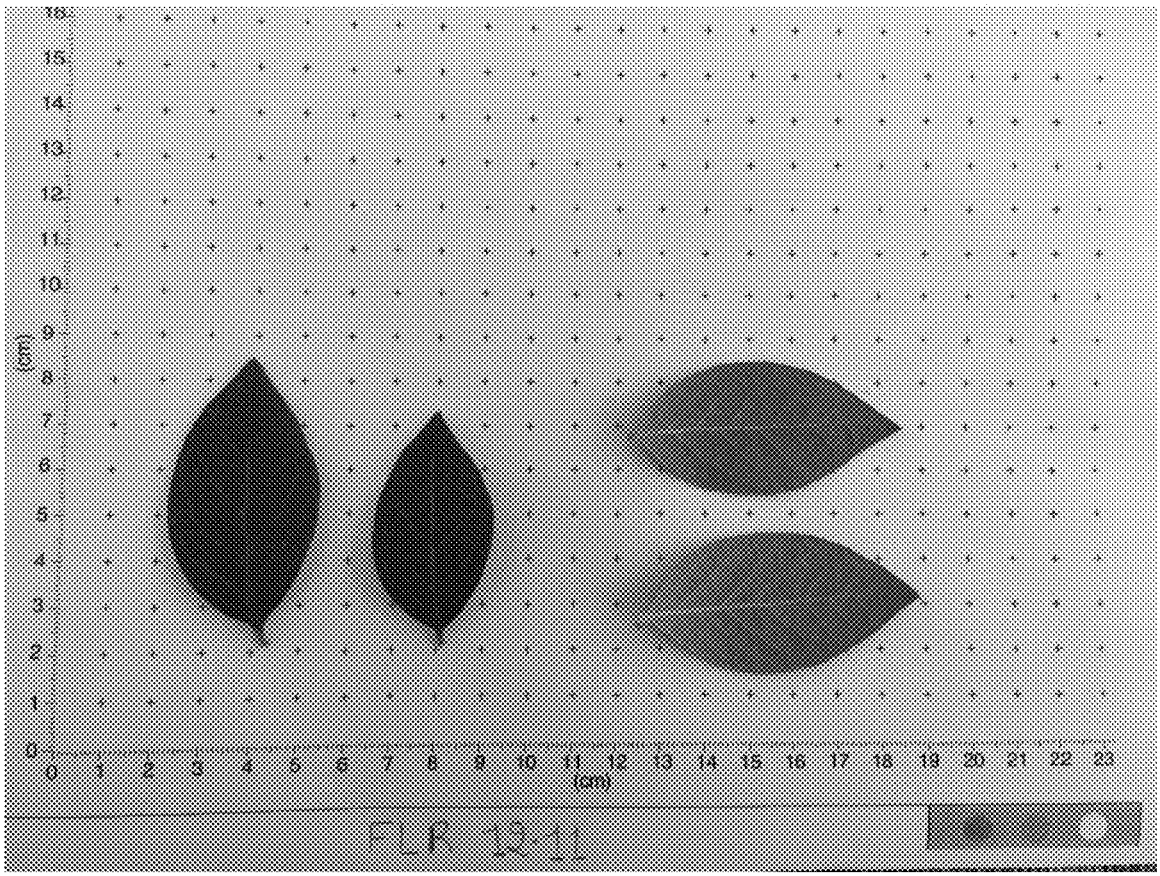
FIG. 4—Shows a close-up of mature 'FLR12-11' leaves with a scale bar.
Figure 5:
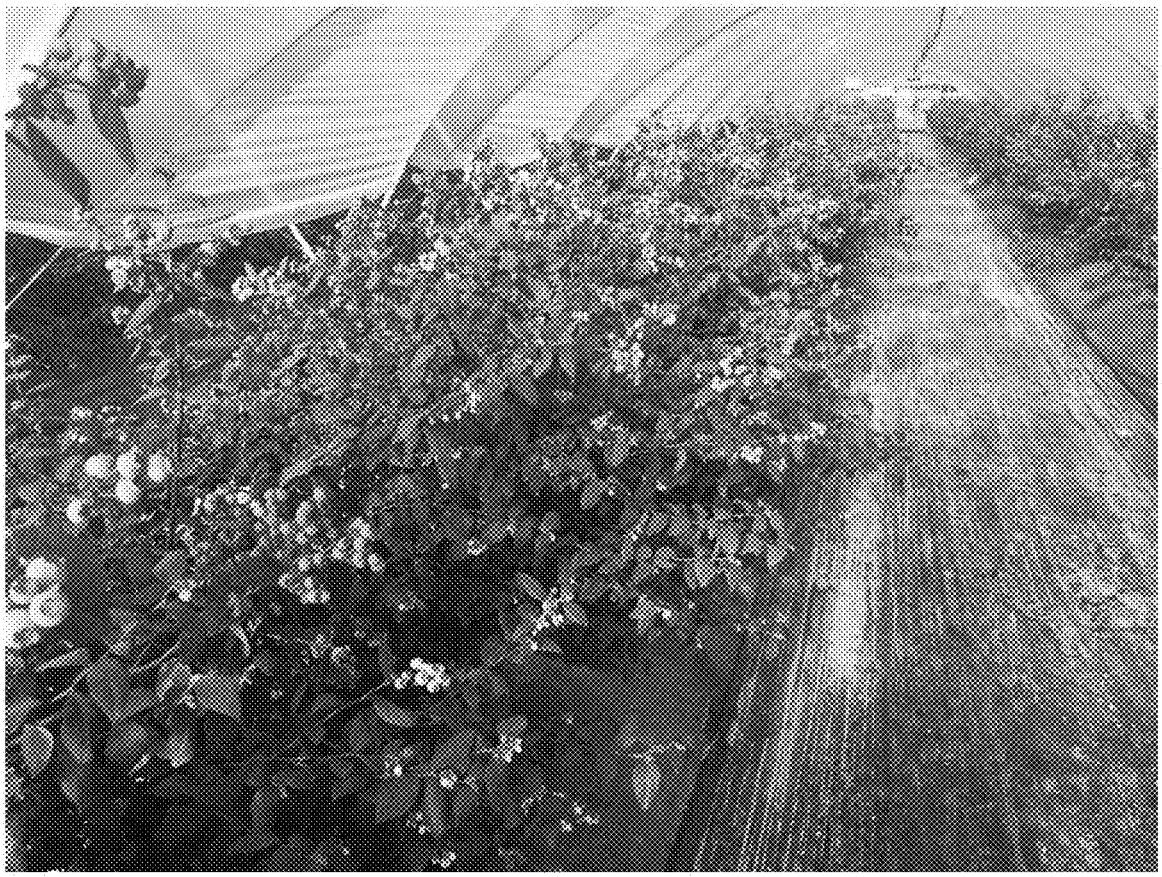
FIG. 5—Shows several 'FLR12-11' plants when grown in an evergreen production system in Lalla Mimouna, Morocco.

The following detailed description sets forth the distinctive characteristics of 'FLR12-11'. The data that define these characteristics were collected from asexual reproductions carried out in Morocco. The plants were 2 years of age when the data was collected. Certain characteristics may vary with plant age. 'FLR12-11' has not been observed under all possible environmental conditions, and the measurements given may vary when grown in different environments. Where means are given, the sample size was 10. Color descriptions are based on The Royal Horticultural Society (R.H.S.) Colour Chart by The Royal Horticultural Society, London, Fifth Edition, 2007. When the R.H.S. color designations differ from the accompanying photographs, the R.H.S. color designations are accurate.

PHENOTYPIC DESCRIPTION OF *VACCINIUM CORYMBOSUM* L. ('FLR12-11')

Plant:

*Plant vigor*.—High.

*Growth habit*.—Semi-upright.

*Flower bud density (number) along flowering twigs in march*.—Medium to High, averaging 8.1.

*Twigginess*.—High.

*Tendency toward evergreenness*.—High.

*Productivity*.—In trials in Morocco, 'FLR12-11' was very productive, with higher total yields than 'Snowchaser'.

*Chilling requirement*.—'FLR12-11' has performed best under evergreen production conditions where chilling is not calculated. 'FLR12-11' flowered and leafed well in areas receiving an average of 300 chill hours (0 to 7° C.).

*Cold hardiness*.—'FLR12-11' has not been grown in temperate climates with extremely cold winter temperatures. Plants have survived winter freezes of −2° C. without damage.

*Ease of propagation*.—In propagation by cuttings of softwood stems, 'FLR12-11' has a good percentage of rooting (80% success), similar to 'Snowchaser'. 'FLR12-11' has also a very good response to meristematic culture.

Trunk and branches:

*Suckering tendency*.—High. Plants typically average 24 canes (with observed number of canes ranging from a minimum of 21 to a maximum of 30) arising from the crown.

*Surface texture (of strong, 6-month-old shoots observed in march)*.—Smooth.

*Surface texture (of 3-year-old and older wood)*.—Rough.

*Color of new twigs observed in the field*.—Yellow-green N144D, with Red 46A on sun-exposed side.

*Color of 3-year-old, rough-textured canes*.—Greyed-brown N199C.

*Internode length (strong, upright shoots measured in march)*.—Mean of 3.53 cm.

Leaves:

*Length (including petiole, from tip of petiole to end of blade)*.—Mean of 8.7 cm.

*Width (at widest point)*.—Mean of 4.4 cm.

*Shape*.—Elliptic.

*Margin*.—Lightly toothed.

*Color*.—Upper surface: Green N137B. Lower surface: Yellow-green N147B.

*Pubescence*.—Upper surface of leaves: Absent. Lower surface of leaves: Absent. Margins: Absent.

*Relative time of leafing versus flowering*.—When grown as an evergreen plant, leafing is after the first flowering wave.

Flowers:

*Arrangement*.—Flowers are arranged alternately along a short, leafless, deciduous branch.

*Fragrance*.—Strong floral fragrance.

*Shape*.—Urceolate.

*Flowering period*.—The bloom period when observed under evergreen production in Morocco is during the month of December

*Cluster (tight, medium, loose)*.—Loose.

*Number of flowers per cluster*.—Mean of 7.7.

*Pedicel*.—Length at time of anthesis: Mean of 9.8 mm. Color at time of anthesis: Yellow-green 144C with Red 46B on the sun-exposed side.

*Peduncle*.—Length at time of anthesis: Mean of 20.4 mm. Color at time of anthesis: Green 142B.

*Calyx*.—Surface texture: Smooth. Diameter: Mean of 7.5 mm. Color (outer surface, visible at the time of anthesis without removing the corolla tube): Green 138C to Red 47B on calyx lobes.

*Corolla*.—Diameter: Mean of 8.18 mm. Length (from pedicel attachment point to corolla tip excluding the pedicel): Mean of 10.7 mm. Aperture diameter: Mean of 5.4 mm. Texture: Smooth. Color: White 155B.

Reproductive organs:

*Style*.—Length (top of ovary to stigma tip): Mean of 8.0 mm. Color: Yellow-green 145B. Location of tip of stigma relative to lip of the corolla — Stigma tip is approximately even to 1 mm outside the corolla lip.

*Anthers*.—Color: Greyed-orange N167B. Pollen — Abundance of shed: Medium. Color: Orange-white 159A.

*Self-fruitfulness*.—Medium to High. Planting in field configurations that promote cross fertilization with other southern highbush varieties is recommended for all southern highbush blueberry plants.

Fruit:

*Mean date of* 50% *harvest in lalla mimouna, morocco*.—March 30.

*Diameter of calyx aperture on mature berry*.—Mean of 9.8 mm.

*Size and shape of calyx lobes on mature berry*.—Small, flat. Medium calyx basin.

*Pedicel length on ripe berry*.—Mean of 11.7 mm.

*Detachment force for ripe berries* (*easy, medium, hard*).—Medium.

*Number of berries per cluster*.—Mean of 8.0.

*Fruiting type*.—On one-year-old and current season's shoots.

Berry:

*Cluster* (*tight, medium, loose*).—Loose.

*Weight* (*on well-pruned plants*).—Mean of 2.7 grams.

*Height*.—Mean of 14.3 mm.

*Width*.—Mean of 20.9 mm.

*Shape*.—Oblate.

*Surface color of mature berries ripe on the plant*.—Violet-blue 98D.

*Surface color of ripe berry after polishing*.—Greyed-purple N186A.

*Immature berry color, with bloom*.—Greyed-green 193B.

*Immature berry color without bloom*.—Yellow-green N144C.

*Surface wax*.—Medium to high. The surface wax on 'FLR12-11' has only moderate persistence.

*Pedicel scar*.—Small and dry. Mean of 3.3 mm.

*Firmness*.—Firm.

*Flavor*.—High level of acidity with a strong aroma.

*Texture*.—Smooth.

Seeds:

*Color of dried seeds*.—Greyed-orange N167A.

*Length of well-developed dried seed*.—Mean of 1.9 mm.

*Width of well-developed dried seed*.—Mean of 1.0 mm.

Use: 'FLR12-11' produces southern highbush blueberries suitable for fresh markets. 'FLR12-11' has performed best in trials when grown under an evergreen management system.

Resistance to diseases, insects, and mites: 'FLR12-11' has grown vigorously and shows excellent bush survival when grown under protected cultivation in an evergreen management system. It appears to be moderately resistant to root rot (*Phytophthora cinnamomi*). 'FLR12-11' appears to have excellent resistance to the fungal species that cause summer leaf spots. Resistance of 'FLR12-11' to fungal leaf spots, *Botrytis* fruit rot, and powdery mildew (*Microsphaera vaccinia*) is greater than that of 'Snowchaser'.

What is claimed is:

1. A new and distinct variety of southern highbush blueberry plant named 'FLR12-11', as illustrated and described herein.

* * * * *